( 12 ) United States Patent
Garvey et al.

(10) Patent No.: US 7,335,333 B2
(45) Date of Patent: Feb. 26, 2008

(54) METHOD OF ALTERING A FLUID-BORNE CONTAMINANT

(75) Inventors: James F. Garvey, Williamsville, NY (US); John A. Lordi, Williamsville, NY (US); Joseph C. Mollendorf, Amherst, NY (US); James D. Felske, Amherst, NY (US)

(73) Assignee: The Research Foundation of the State University of New York, Albany, NY (US)

( * ) Notice: Subject to any disclaimer, the term of this patent is extended or adjusted under 35 U.S.C. 154(b) by 155 days.

(21) Appl. No.: 10/765,807

(22) Filed: Jan. 27, 2004

(65) Prior Publication Data

US 2004/0184907 A1 Sep. 23, 2004

Related U.S. Application Data

(60) Provisional application No. 60/486,507, filed on Jul. 11, 2003, provisional application No. 60/445,979, filed on Feb. 7, 2003.

(51) Int. Cl.
*A61L 2/00* (2006.01)
(52) U.S. Cl. ............................ 422/33; 422/28; 422/125
(58) Field of Classification Search .................... 422/4, 422/125, 28, 33
See application file for complete search history.

(56) References Cited

U.S. PATENT DOCUMENTS

| 2,691,482 | A | * | 10/1954 | Ungar ............................ 418/1 |
| 3,222,883 | A | | 12/1965 | Glaspie |
| 3,549,278 | A | | 12/1970 | Giddings |
| 3,555,787 | A | * | 1/1971 | Lustig .......................... 96/124 |
| 3,917,168 | A | | 11/1975 | Tenney |
| 3,966,407 | A | * | 6/1976 | Zuckerberg et al. ............ 422/4 |
| 4,865,749 | A | * | 9/1989 | Yoshida ....................... 210/742 |
| 5,271,557 | A | | 12/1993 | Lynch et al. |
| 5,979,075 | A | * | 11/1999 | Grenci et al. .................. 34/410 |
| 6,280,691 | B1 | * | 8/2001 | Homeyer et al. ............ 422/122 |
| 6,312,240 | B1 | | 11/2001 | Weinbrecht |
| 2004/0002126 | A1 | * | 1/2004 | Houde et al. ............... 435/7.32 |

FOREIGN PATENT DOCUMENTS

| EP | 0 821 972 | 2/1998 |
| FR | 2 758 987 | 8/1998 |
| WO | WO 96/02281 | 2/1996 |

OTHER PUBLICATIONS

"NASA Compressor Thermodynamics", www.grc.nasa.gov/WWW/K-12/airplane/compth.html, www.grc.nasa.gov/WWW/K-12/airplane/specheat.html.*
Dictionary definition of infection The American Heritage® Dictionary of the English Language, Fourth Edition Copyright © 2004, 2000 by Houghton Mifflin Company. Published by Houghton Mifflin Company. All rights reserved.*

* cited by examiner

*Primary Examiner*—Gladys J P Corcoran
*Assistant Examiner*—Sean E. Conley
(74) *Attorney, Agent, or Firm*—Jaeckle Fleischmann & Mugel, LLP

(57) ABSTRACT

An improved method of altering a fluid-borne contaminant includes the steps of: providing a positive-displacement pump (21) having an inlet (22) and an outlet (23); connecting the pump inlet to a source (24) of contaminated fluid; operating the pump at a pressure ratio sufficient to elevate the pressure and temperature of the fluid and contaminants passing through the pump to alter or convert substantially all of the contaminants passing through the pump.

5 Claims, 5 Drawing Sheets

METHOD OF ALTERING A FLUID-BORNE CONTAMINANT

CROSS-REFERENCE TO RELATED APPLICATIONS

This application claims the benefit of the earlier filing dates of prior pending U.S. provisional patent applications No. 60/445,979, filed Feb. 7, 2003, and No. 60/486,507, filed Jul. 11, 2003.

TECHNICAL FIELD

The present invention broadly provides an improved method of altering a fluid-borne contaminant, and, more particularly, to an improved method for efficiently altering or converting a particulate, chemical or biological contaminant in a compressible gas stream to a less-objectionable form.

BACKGROUND ART

The events of Sep. 11, 2001 have demonstrated that we live in a new era. Terrorists have demonstrated a willingness and ability to attack governmental and civilian infrastructure. Some of these attacks are physically destructive of the infrastructure, whereas others are intended to deny the use of a facility.

For example, one will readily recall the threat of anthrax scares that followed the events of September 11th. In some cases, those anthrax scares involved distribution of anthrax spores through the postal service to unwitting recipients. In another instance, certain Senate office buildings were found to contain anthrax spores. This denied the government the use of these buildings during a period of remediation and cleaning.

Accordingly, it would be generally desirable to provide an improved method of altering a fluid-borne contaminant to a less-objectionable form.

DISCLOSURE OF THE INVENTION

With parenthetical reference to the corresponding parts, portions or surfaces of the disclosed embodiment, merely for purposes of illustration and not by way of limitation, the present invention broadly provides an improved method of altering a fluid-borne contaminant.

The improved method broadly includes the steps of: providing a positive-displacement pump (21) having an inlet (22) and an outlet (23); connecting the pump inlet to a source (24) of contaminated fluid; operating the pump at a pressure ratio sufficient to elevate the pressure and temperature of the fluid and contaminants passing through the pump to alter substantially all of the contaminants passing through the pump.

The contaminants may be altered by chemical reduction, oxidization, combustion, heating, passivation, or some other process or means. As used herein, the terms "alter" and "convert" are intended to generically include any and all of such processes and means.

The contaminants may include particulate material (e.g., asbestos, etc.), a biological agent (e.g., a spore, a bacteria, a virus, a pathogen, a fungus, a pollen, etc.), or some other substance. The fluid should include a compressible gas. The fluid may be entirely gaseous, or only partially gaseous. The contaminants may be entrained in the gas, or may be present in a liquid mixed with such gas.

The pump may be a Roots-type positive displacement pump, a compressor, a piston-and-cylinder, or the like. The pressure ratio of the pump is the pressure at the pump outlet divided by the pressure at the pump inlet.

The time of passage may be controlled by restricting the flow of fluid and contaminants passing through the pump, and/or any associated upstream or downstream elevated temperature portion.

The temperature of the fluids and contaminants should be heated to at least about 200° C. at the pump outlet.

The improved method may further include the additional steps of: providing a catalytic converter, and causing the flow of gas to pass sequentially through the pump and the catalytic converter. The catalytic converter may be arranged downstream of a pump, but this arrangement need not invariably obtain.

In another form, a series of pumps may be arranged so as to be in series with one another. Contaminated fluid from the source is caused to pass sequentially through the pumps so as to alter the contaminants by multi-recompressive heating.

In one arrangement, the method includes the additional step of: preheating the temperature of the fluid entering the pump with heat provided from the temperature of fluid exiting the pump.

If desired, a fuel or reagent can be entrained in, or atomized with, the fluid supplied to the pump.

The method may further comprise the additional steps of: sampling the fluid exiting the pump to determine the extent to which contaminants therein have been altered; and adjusting the operation of the pump (i.e., so as to selectively increase the temperature and/or the time of passage) so that substantially all of the contaminants will be altered or converted by passing such contaminated fluid through the pump.

In another aspect, the invention provides an improved method of altering a fluid-borne contaminant, which method includes the steps of: providing a positive-displacement pump having an inlet and an outlet; connecting the pump inlet to a source of contaminated fluid; operating the pump so as to elevate the temperature of the fluid and contaminants passing through pump to at least about 200° C.; and controlling the time during which the temperature of the fluid and contaminants are elevated; thereby to alter substantially all of the contaminants passing through the pump.

Accordingly, the general object of the invention is to provide an improved method of altering a fluid-borne contaminant.

Another object is to provide an improved method of selectively and controllably altering a fluid-borne contaminant, such as a particulate material, a biological agent (e.g., a spore, a bacteria, a virus, a pathogen, a fungus, a pollen, etc.), a chemical agent, some other substance, or a combination thereof.

Still another object is to provide an effective and low-cost method of remediating a contaminated fluid.

Still another object is to provide an improved method of compressively heating a volume of gas, substantially uniformly and substantially instantaneously.

These and other objects and advantages will become apparent from the foregoing and ongoing written specification, the drawings, and the appended claims.

DESCRIPTION OF THE PREFERRED EMBODIMENTS

Figure 1:
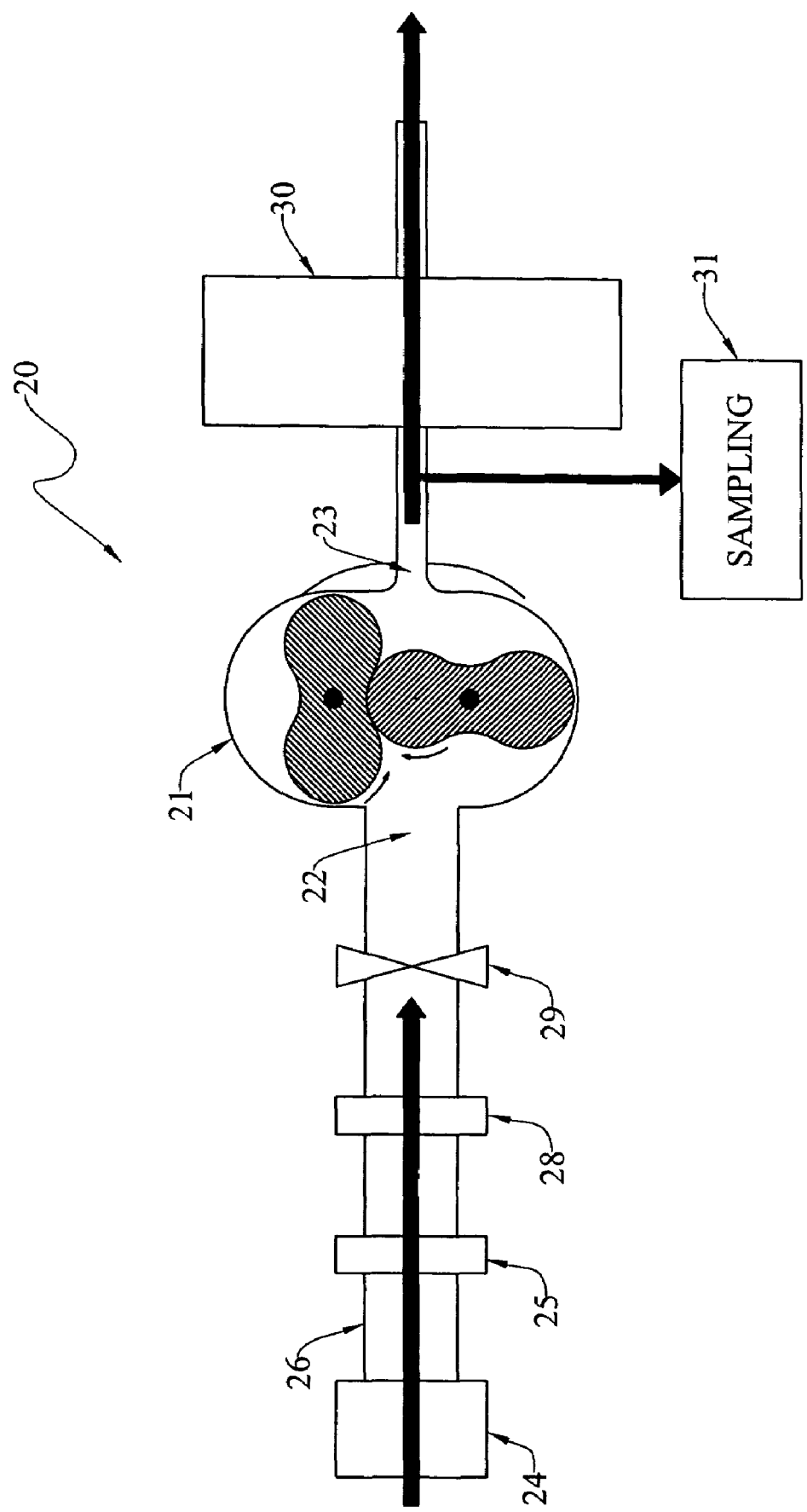
FIG. 1 is a schematic of one form of apparatus for performing the improved method.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

The present invention broadly provides an improved method of altering or converting a fluid-borne contaminant from one form to another. The improved method uses apparatus that is, for all intents and purposes, old, albeit such apparatus was not previously used for the purpose herein disclosed and intended. Indeed, the improved method deliberately misuses that known apparatus to achieve objectives that were avoided in the prior art.

The improved method utilizes the equation of state for an ideal gas:

$$pV=nRT$$

where p is pressure, V is volume, n is the mass of the gas expressed in moles, R is the universal gas constant [i.e., R=8.314 joule/(mole)(K°)=1.986 cal/(mole)(K°)], and T is the temperature (expressed in degrees Kelvin).

The invention provides an improved method of altering or converting a fluid-borne contaminant, which method comprises or includes the steps of: providing a positive-displacement pump having an inlet and an outlet; connecting the pump to a source of contaminated fluid; and operating the pump at a pressure ratio sufficient to elevate the pressure and temperature of the fluid and contaminants passing through the pump; thereby to substantially alter all of the contaminants passing through the pump.

As used herein, the word "contaminant" is intended broadly and generically. It may include a particulate contaminant, such as an asbestos particle or the like. It may include a biological agent such as a pathogen, pollutant, virus, fungus, mold, spore, or the like. It may include some other chemical, pollutant or contaminant. At least a portion of the fluid should be compressible. This fairly means that the fluid should have a gaseous component, if the fluid is not wholly gas. As used herein, the word "fluid" is generic to either a liquid or a gas.

The improved method operates to volumetrically compress the gas, causing a substantially uniform increase in its temperature very quickly. The pump may be a Roots-type positive displacement pump or blower, a compressor, a piston-and-cylinder, or some other similar device. As used herein, a Roots-type positive displacement pump, sometimes known as a Roots Blower, refers to a device having two multi-lobed rotors or impellers arranged within an elongated casing or housing. The rotors or impellers are rotated in opposite directions, and closely interfit with one another, the angular walls of the casing, and the end walls of the casing. As each impeller lobe passes by the inlet, it traps a defined volume of gas and compresses it as it is carried around to the outlet, where it is discharged. Examples of such Roots-type devices are representatively shown and described in U.S. Pat. Nos. 4,215,977, 4,390,331, 5,040,959, 4,652,223, 4,666,384, 4,666,385, 4,859,158, 4,975,032 and 5,702,240, the aggregate disclosures of which are hereby incorporated. The use of such Roots-type devices to compressively heat a gas is disclosed in a doctoral dissertation of David Blekhman, "A Theoretical and Experimental Study of High-temperature Compressive Gas Heating", Department of Mechanical and Aerospace Engineering, State University of New York at Buffalo, dated Jul. 16, 2002.

In one form, multiple pumps may be placed in series such that the fluid-to-be-treated is caused to pass sequentially through these pumps, and be successively treated by each elevation of temperature. As used herein, the pressure ratio is the pressure at the output of the pump divided by the pressure of the input of the pump. The time during which such fluid and contaminants are subjected to an elevated temperature may be regulated or monitored by means of adjusting the flow of contaminants through the apparatus, or by providing a heated tube downstream of the pump. It is presently preferred that the pump be operated at a pressure ratio of at least 2.0, or that the temperature of the outlet gas be at least about 200° C. at the pump outlet. In one experiment upwards of 99.9% of *Bacillus globigii* (Bg) spores, an anthrax simulant, where killed by heating to about 200° C. in a single pass through a Roots-type positive displacement pump.

Referring now to the drawings, and, more particularly, to FIG. 1 thereof, a test bed arrangement of the present apparatus is generally indicated at 20. This device is shown as having a Roots-type pump or compressor 21, and an inlet 22 and an outlet 23. Contaminated fluid from a suitable source 24 is provided through a high-flow filter 25 to an inlet pipe 26, containing a lambda-square orifice flow meter 28 and a throttling valve 29 to the pipe inlet 22. In the pump, the volume of the inlet fluid is compressed, and is discharged through the pump outlet 23 through a muffler or silencer 30. A portion of the fluid outlet stream is sampled, as indicated by block 31.

Figure 2:
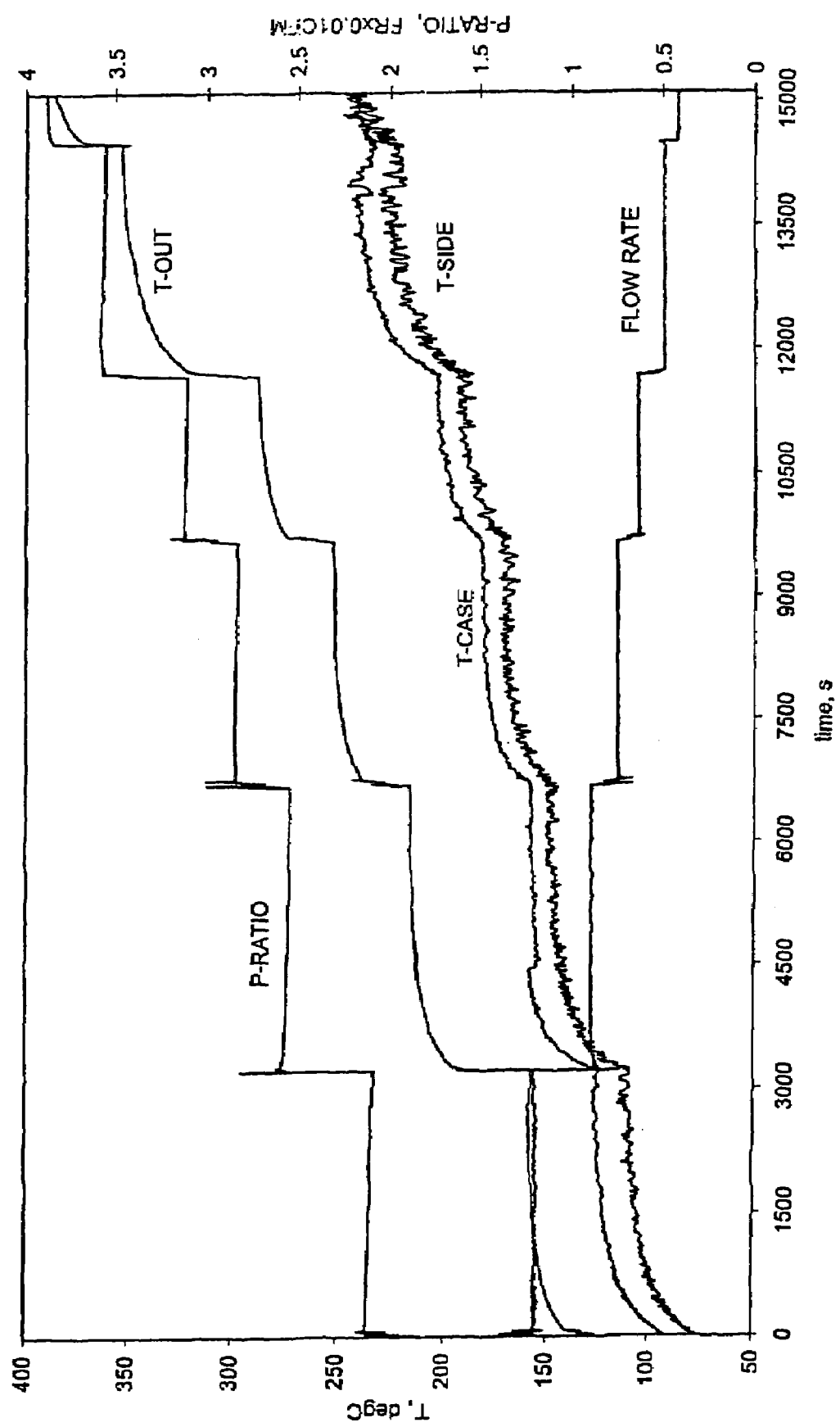
FIG. 2 is a plot of temperature (left ordinate) and pressure ratio (right ordinate) versus time (abscissa), showing that the increase in temperature is substantially in-phase with a step change in pressure ratio.

FIG. 2 is a plot showing temperature (left ordinate) and pressure ratio (right ordinate) versus time. It should be noted that as the pressure ratio is increased, as represented by the step functions occurring at about 3300 seconds, 6500 seconds, 9500 seconds, 11500 seconds and 14000 seconds, respectively, there is a substantially in-phase substantially-instantaneous corresponding rise in the outlet temperature, represented by the curve labeled $T_{out}$. At the same time, the flow through the pump is stepped downwardly.

Figure 3:
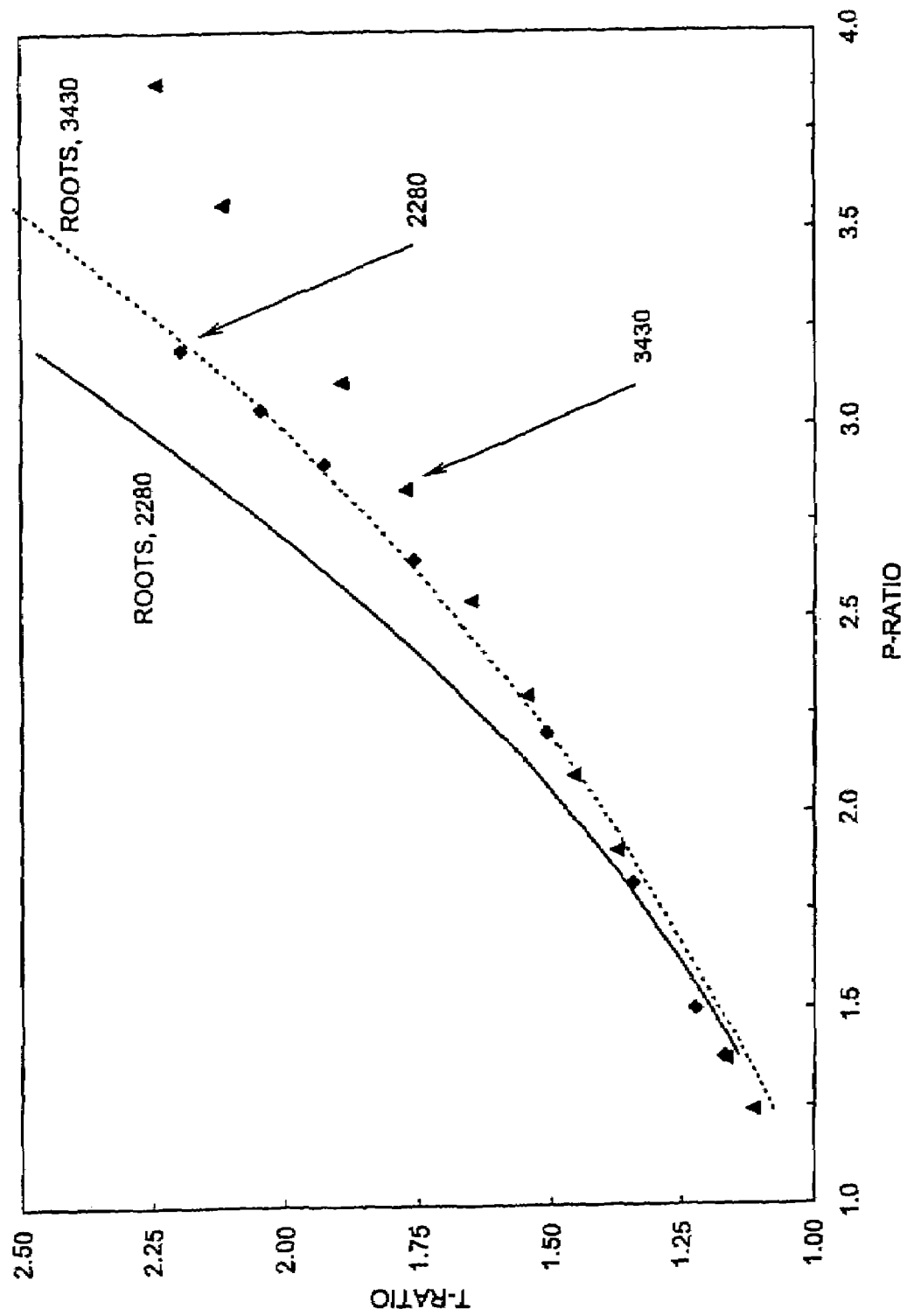
FIG. 3 is a plot of temperature ratio versus pressure ratio for a Roots-type pump or blower operated at two different rpms.

FIG. 3 is a plot of temperature ratio versus pressure ratio for a Roots blower, such as shown FIG. 1, albeit operated at two different angular speeds. This curve illustrates that as the pressure ratio increases, the temperature ratio also increases, albeit in a non-linear manner.

Figure 4:
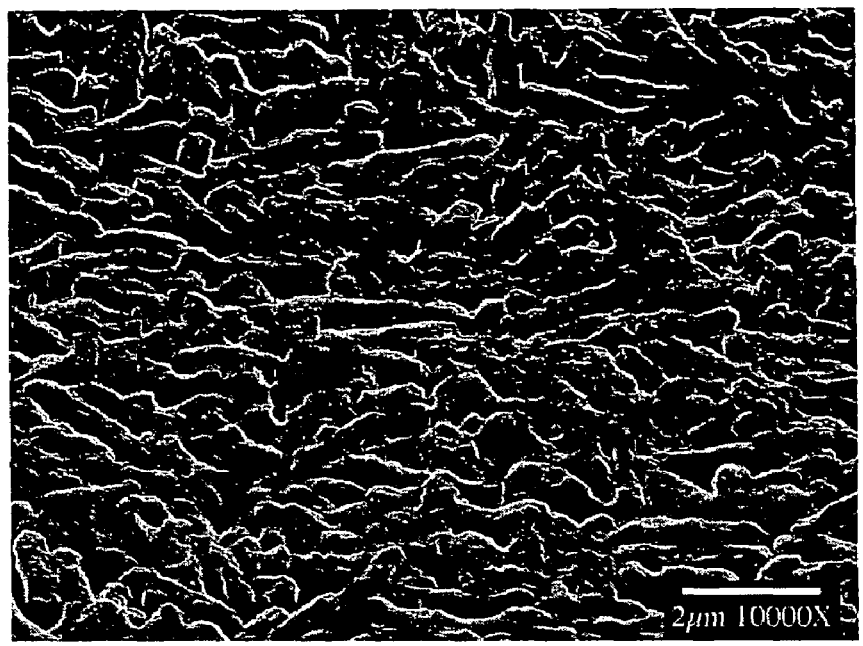
FIG. 4 is a scanning electron micrograph of a test sample of air contaminated with *Bacillus globigii* (Bg) spores, prior to passing through the apparatus.

FIG. 4 is a scanning electron micrograph showing a test sample containing a large number of Bg spores in a contaminated fluid sample provided to the inlet of the pump.

Figure 5:
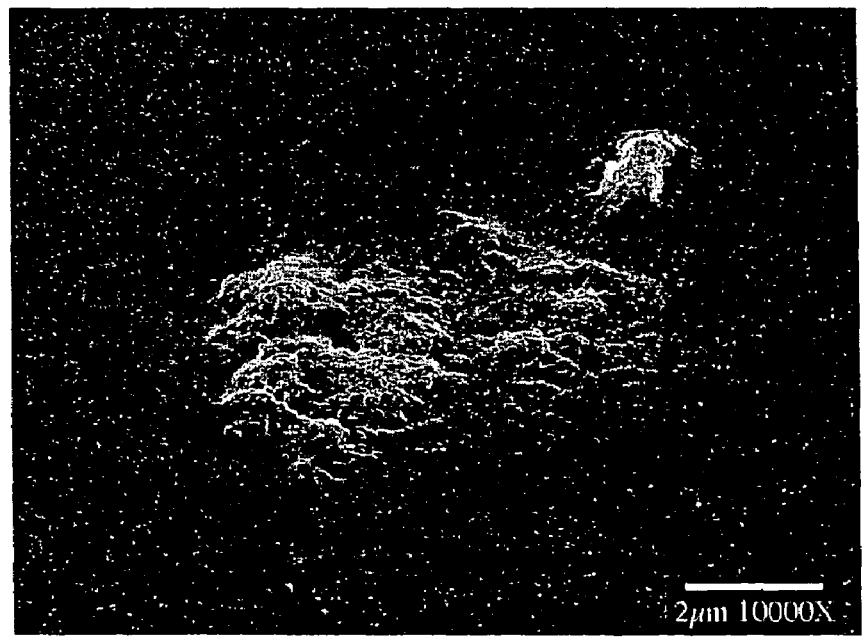
FIG. 5 is a scanning electron micrograph image showing the contaminated air depicted in FIG. 4, after having passed through the apparatus with compressive heating at a temperature above about 200° C.

FIG. 5 is a scanning electron micrograph of the flow at the fluid outlet. These pictures depict a handful of residue Bg spores. However, when these were attempted to be cultured and grown, it was found that these spores were dead. Thus, these are not live spores, but dead residue Bg spores.

Figure 6:
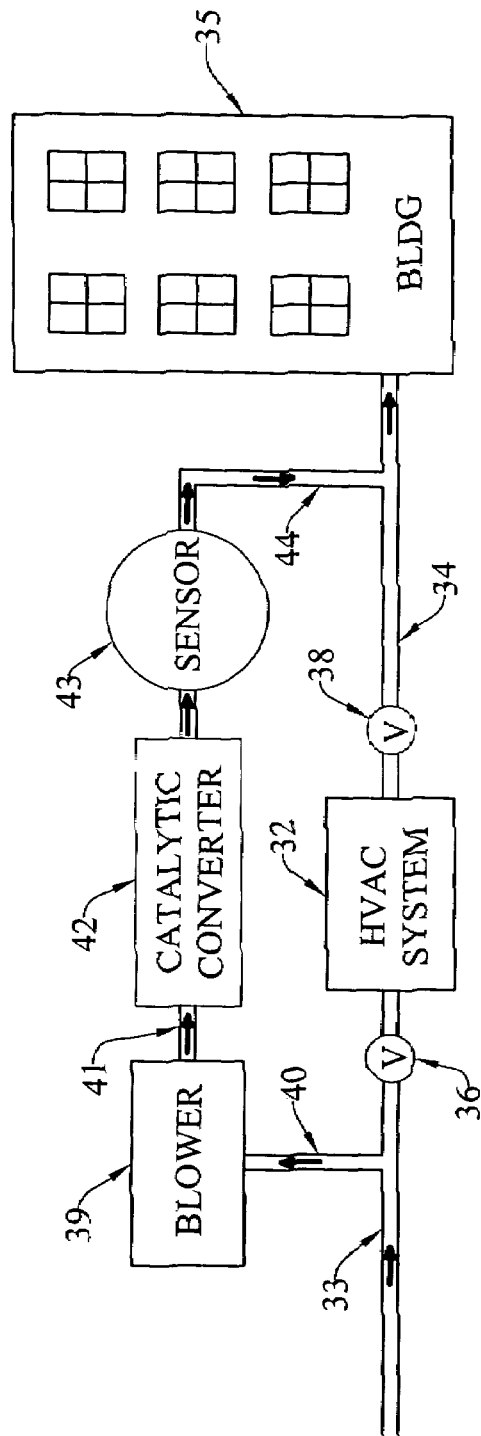
FIG. 6 is a schematic view showing the improved apparatus arranged parallel with a conventional HVAC system used in association with a building.

FIG. 6 is a schematic showing the improved apparatus as being operatively arranged in parallel with a conventional HVAC system 32 having an inlet 33 and an outlet 34 arranged to supply the outlet flow to a building 35. In this case, there are two valves, 36 and 38 arranged upstream and downstream, respectively, of the HVAC system. Pump 39 is provided through an inlet 40, and having an outlet 41. The outlet from the pump is provided to a catalytic converter 42 for conversion or alteration of the particular contaminant. A sensor 43 is arranged to sense the presence of contaminant in the outlet flow provided in outlet conduit 44, which is also provided to the building. Thus, valves 36 and 38 can be opened, and pump 39 disabled so as to permit normal use of the HVAC system. However, in the event of an emergency, or upon some other triggering event, valves 36 and 38 may be selectively closed to divert flow to the pump and catalytic converter, for treatment of the fluid contained therein. In an alternative arrangement, the catalytic converted could be positioned upstream of the pump.

Figure 7:
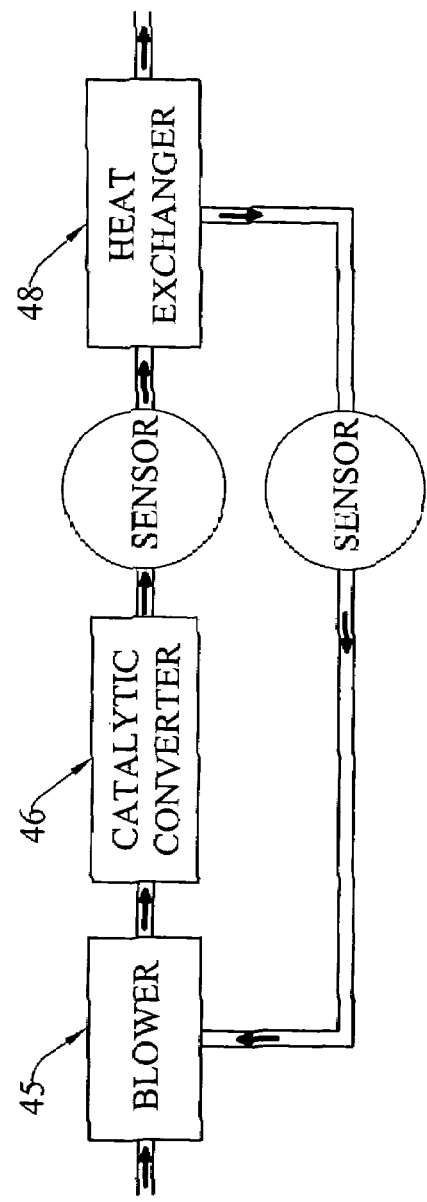
FIG. 7 is a schematic view showing a downstream sensor as used to adjust the operation of the blower so as to alter or convert substantially all of the contaminants therein.

FIG. 7 is a schematic view showing another form of the pump, this time indicated at 45, and catalytic converter 46 associated with a heat exchanger 48. The function of heat exchanger 48 is to extract heat from the outlet flow, and to provide such heat back to preheat the inlet flow to the pump.

Therefore, the present invention broadly provides an improved method of altering a fluid-borne contaminant, which method includes the steps of: providing a pump having an inlet and outlet; connecting the pump inlet to a source of contaminated fluid; operating the pump at a pressure ratio of at least 2.0 so as to sufficiently elevate the temperature of the fluid and contaminants passing through the pump; and controlling the time during which the temperature of the fluid and contaminants are elevated; thereby to alter substantially all of the contaminants passing through the pump.

In another form, the invention provides an improved method of altering a fluid-borne contaminant, which includes the steps of: providing a pump having an inlet and outlet; connecting the pump inlet to a source of contaminated fluid; operating the pump so as to elevate the temperature of the fluid and contaminants passing through the pump to at least 200° C. and controlling the time during which the temperature of the fluid and contaminants are elevated, thereby to alter substantially all of the contaminants passing through the pump.

In the foregoing methods, the contaminants may be particulate or biological. The contaminants may be altered by chemical reduction, oxidization or combustion. The fluid must contain a compressible gas. However, the entire inlet flow need not to be gaseous in nature. The contaminants may be entrained in the gas. In other form, a fuel or reagent may be entrained in, or provided as an aerosol, to the gas. The pump may be Roots-type positive displacement pump, a compressor, a piston-and-cylinder, or some other type. As demonstrated above, the outlet flow from the pump may be provided to a catalytic converter, or may be caused to pass through another pump. Heat at the pump outlet may be extracted and feed back preheat the gas provided to the pump inlet. The fluid at the pump outlet may be sampled to determine the existing level of contamination, and the operation of the pump may be adjusted so that substantially of the contaminants are converted by passing through the pump.

Therefore, while two presently preferred forms of the improved method have been shown and described, and various changes and modifications thereof discussed, persons skilled in this art will readily appreciate that various additional changes and modifications may be made without departing from the spirit of the invention, as defined and differentiated by the following claims.

What is claimed is:

1. A method for killing at least 99.9% of the anthrax spores in a fluid, comprising the steps of:
   a) passing a fluid containing anthrax spores through one positive-displacement pump or through multiple positive-displacement pumps connected in series; and,
   b) operating the one positive-displacement pump or multiple positive-displacement pumps connected in series at a pressure ratio or pressure ratios such that the passage of the fluid containing anthrax spores through the one positive-displacement pump or through the multiple positive-displacement pumps connected in series kills at least 99.9% of the anthrax spores in the fluid.

2. The method of claim 1, wherein the one positive displacement pump or at least one of the multiple positive-displacement pumps connected in series is operated at a pressure ratio exceeding the recommended operating pressure limitations for the one positive displacement pump or at least one of the multiple positive-displacement pumps connected in series.

3. The method of claim 1, wherein the one positive displacement pump or at least one of the multiple positive-displacement pumps connected in series is operated at a pressure ratio of at least 2.0.

4. The method of claim 1, wherein the one positive displacement pump or at least one of the multiple positive-displacement pumps connected in series is operated at a pressure ratio sufficient to raise the temperature of the fluid containing biological contaminants passing through the one positive displacement pump or at least one of the multiple positive-displacement pumps connected in series to at least 200° C.

5. A method for killing at least 99.9% of the anthrax spores in a fluid, comprising the steps of:
   a) passing a fluid containing anthrax spores through a positive-displacement pump; and,
   b) operating the positive-displacement pump at a pressure ratio of at least 2.0 such that the passage of the fluid containing anthrax spores through the positive-displacement pump kills at least 99.9% of the anthrax spores in the fluid.

* * * * *